United States Patent [19]

Reel et al.

[11] Patent Number: 4,512,986
[45] Date of Patent: Apr. 23, 1985

[54] PROGRESTATIONALLY ACTIVE STEROIDS

[75] Inventors: Jerry R. Reel, Cary; Clarence E. Cook, Chapel Hill, both of N.C.

[73] Assignee: Research Triangle Institute, Research Triangle Park, N.C.

[21] Appl. No.: 517,457

[22] Filed: Jul. 26, 1983

[51] Int. Cl.$^3$ .............................................. C07J 5/00
[52] U.S. Cl. .................................. 514/170; 260/397.3; 514/177
[58] Field of Search ...................... 260/397.3; 424/238

[56] References Cited

U.S. PATENT DOCUMENTS

| | | | |
|---|---|---|---|
| 3,528,999 | 9/1970 | Bladon et al. | 260/379.3 |
| 3,636,011 | 1/1972 | Phillipps et al. | 260/397.3 |
| 3,705,179 | 12/1972 | Marshall et al. | 260/349 |
| 3,846,456 | 11/1974 | Campbell et al. | 260/397 |
| 4,002,746 | 1/1977 | Hughes et al. | 424/243 |
| 4,139,617 | 2/1979 | Grunwell et al. | 424/238 |
| 4,150,126 | 4/1979 | Fex et al. | 424/238 |
| 4,176,126 | 11/1979 | Annen et al. | 260/397.45 |
| 4,239,681 | 12/1980 | Grunwell et al. | 260/239 |
| 4,265,815 | 5/1981 | Varma | 260/239 |
| 4,278,668 | 7/1981 | Gueritee | 424/238 |

*Primary Examiner*—Elbert L. Roberts
*Attorney, Agent, or Firm*—Cushman, Darby & Cushman

[57] ABSTRACT

Novel steroids having the formula

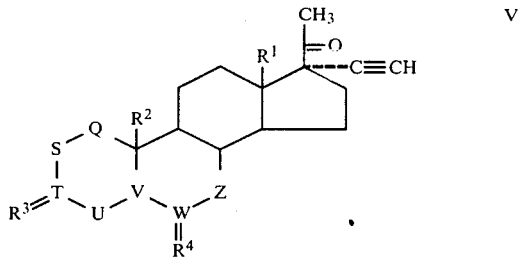

wherein
$R^1$ is selected from the group consisting of methyl, ethyl, and propyl;
$R^2$ is selected from the group consisting of H and methyl;
$R^3$ is selected from the group consisting of OXO and H(OR$^5$);

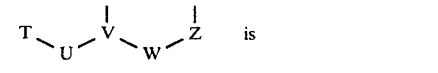

is

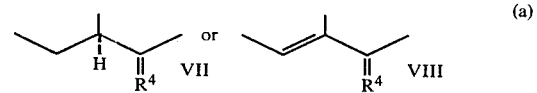

wherein $R_4$ is selected from the group consisting of $H_2$, H(methyl), H(Cl), H(F), and $=CH_2$; or

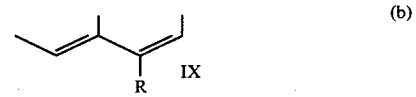

wherein R is selected from the group consisting of H, methyl, Cl, and F. Q-S is selected from the group consisting of —CH=CH— and —CH$_2$CH—.

Also disclosed is a method for making and therapeutically using the steroids and for making the intermediates.

41 Claims, No Drawings

PROGRESTATIONALLY ACTIVE STEROIDS

FIELD OF THE INVENTION

This invention relates generally to the field of steroids and, in particular, to a new class of 17α-ethynylprogesterones which exhibits progestational activity.

BACKGROUND OF THE INVENTION

The term "progestational" means "preceding gestation" and some known progestational agents stimulate a condition of pseudopregnancy. Thus these agents are useful as contraceptives and in the treatment of disorders associated with menstrual irregularities. Most known progestational agents are not produced by the human body but yet function in a manner similar to natural gestagens (e.g. progesterone). Thus much research time and resources have been devoted to developing progestational compounds having high potency (i.e., which may accordingly be administered in small amounts and yet be effective) and relatively low, if any, side effects. Progestational activity is generally determined by the so-called Clauberg assay wherein a compound whose activity is to be evaluated is administered to estrogen-primed female rabbits and glandular development of the uterine endometrium is scored on a 0 to +4 basis according to the McPhail scale (Kirk-Othmer, *Encyclopedia of Chemical Technology*, 3rd Edition, Volume 12, Wiley-Interscience).

Perhaps the best known gestagen is progesterone, a naturally occurring hormone formed in the adrenals, ovaries, and placenta and which is the major female sex hormone required for the maintenance of pregnancy. Progesterone is a 21-carbon steroid secreted by the corpus luteum and which has the following structure wherein the numbering system and alphabetic ring designation system conventionally used when naming derivatives not having well known trivial names is shown:

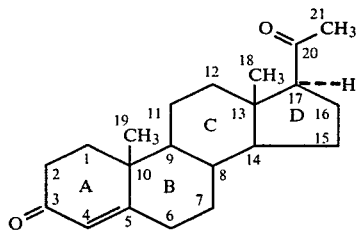

where, as will be the convention throughout the specification and claims, substituents attached to the ring system from above are designated β and represented by a solid line while substituents attached from below are designated α and represented by a dashed line.

Synthetic progesterone is readily available (e.g., from the Upjohn Company, Kalamazoo, Mich.). Progesterone is only weakly active when taken orally, however, and has been replaced almost entirely by more active oral gestagens.

Molecular biologists and endocrinologists have now established the principal features of the molecular mechanisms involved in steroid hormone action (see Receptors and Hormone Action, Ed. B. W. O'Malley and L. Birnbaumer, Vols. I and II, Academic Press, N.Y., 1978). For hormonal action to occur the steroid hormone must enter the endocrine-responsive cell. Endocrine-responsive cells are characterized by possessing, both in the cytoplasm and in the nucleus, a specific protein with high binding affinity for the steroid hormone known as the "hormone receptor protein" or simply as "receptor protein". Such receptor proteins are characterized by their high specificity for the steroid and by their capacity to distinguish through their binding affinities very small structural differences between steroids.

DESCRIPTION OF PRIOR ART

Excluding the corticoids, three structural types dominate the steroid market:

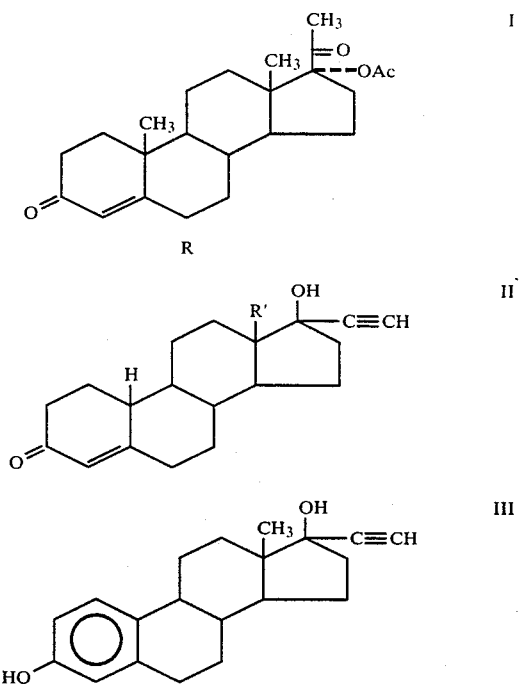

17α-Acetoxyprogesterone type. These compounds find wide utility as progestational agents, as contraceptives, in veterinary use for synchronization of estrus in feed-lot cattle, for inhibiting estrus in the domestic pet, for treatment of certain hyperplasias such as benign prostatic hypertrophy, prostatic cancer, breast cancer and as antiandrogenic agents. Medroxyprogesterone acetate (I; R=CH$_3$) presently dominates the market.

19-Norethisterone. This compound (II; R'=methyl), and its 18-methyl derivative (II; R'=ethyl) dominate the contraceptive markets of the world, when they are generally employed in conjunction with ethinylestradiol (III). They are potent progestational agents, androgenic agents, etc.

17α-Ethinylestradiol (III). This compound and its 3-methyl ether (mestranol) are virtually the only orally active estrogens presently used in contraceptives.

Compounds of types (I) and (II) are good progestational agents but, as is common with many materia medica, possess some undesirable side effects which stem from their characteristic structural features. Thus, for example, the 17α-acetoxyprogesterone (I; R=methyl) series of progestational agents show a greater incidence of spontaneous mammary tumors in the experimental animal than do derivatives of 19-norethisterone (II) [See for example Report of the Committee on Safety of Medicine, H.M.S. Stationary Office, 1972, U.K.; *Toxicol. Applied Pharmacol.*, 37, 181 (1976)]. Also 17α-acetoxyprogesterone shows a higher rate of thromboembolic episodes in contraceptive preparations than do corresponding preparations of (II) (see, for example, Inwan et al., Brit. Med. J. (2) 203 [1970]).

The 19-norsteroids (II) in contrast may cause hypertension (Lancet, i, 624 [1977]). As 17-alkylated derivatives of testosterone, they cause BSP retention indicating interference with liver function. They are also strong androgens (see *Int. Encycl. Pharmacol. Therap.* Section 48, Vol. II, p. 4333 and 113).

SUMMARY OF THE INVENTION

This invention provides for the first time, 17β-acetyl-17α-ethynyl steroids which combine, in one single molecule, the structural characteristics of both 17α-acetoxy-17β-acetyl-(I) and 17β-hydroxy-17α-ethynyl (II) steroids. The invention further provides a novel synthetic route to 17β-acetyl-17α-ethynyl steroids. The inventors have found that, in contradistinction to (II), the novel structures of the present invention are free from undesirable androgenicity as determined by binding affinity to androgen receptor. They have also made the discovery that certain of these novel structures possess high binding affinities for the progesterone receptor and potent progestational activity.

This invention, more specifically, relates to novel steroidal structures which possess in a single molecule the unique structural features characteristic of both (I) and (II) as indicated in partial formula (IV)

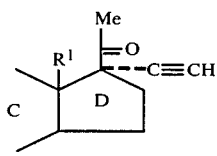

IV (where $R^1$ is as hereinunder defined), which compounds have not hitherto been described in the art, to a new method for their preparation, to their use as therapeutic agents, and to pharmaceutical preparations thereof.

The specific preferred embodiments subsequently to be detailed herein as well as other embodiments intended to be within the scope of the invention may be generally set forth as follows:

(a) a steroid having the formula

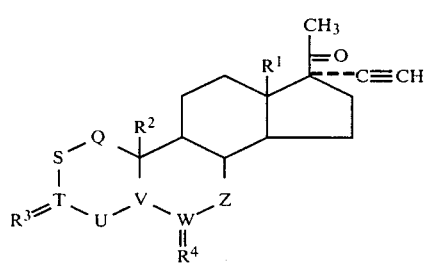

V and (b) a steroid having the formula

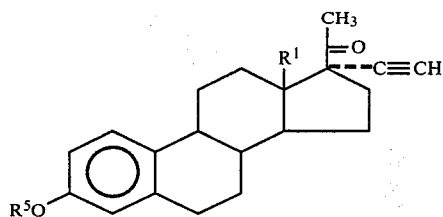

VI wherein $R^1$ is selected from the group consisting of methyl, ethyl, and propyl;

$R^2$ is selected from the group consisting of H and methyl;

$R^3$ is selected from the group consisting of oxo and $H(OR^5)$;

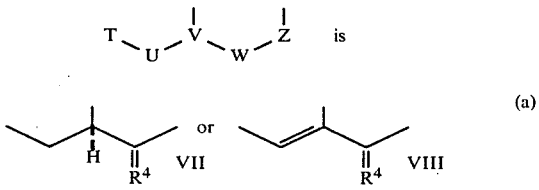

(a)

wherein $R^4$ is selected from the group consisting of $H_2$, H(methyl), H(Cl), H(F), and =$CH_2$; or

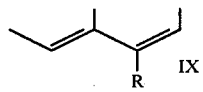

(b)

wherein R is selected from the group consisting of H, methyl, Cl, and F;

$R^5$ is H or a pharmaceutically acceptable substituent selected from the group consisting of:

acyl having from 1 to 12 carbon atoms, 2-tetrahydropyranyl, 4-tetrahydropyranyl, 1-cycloalkyl having from 5 to 7 carbon atoms, 1-methoxycycloalkyl and 1-ethoxycycloalkyl in which the cycloalkyl group has from 5 to 7 carbon atoms, cycloalkylcarbonyl wherein the cycloalkyl group has from 5 to 10 carbon atoms, benzoyl, phenacetyl, 1-adamantylcarbonyl, and 1-cyclopentylcarbonyl; and Q-S is selected from the group consisting of —CH=CH— and —CH$_2$—CH$_2$—.

In the above generic formulation, as well as in the rest of the specification and in the claims, "$H_2$" is intended to denote to hydrogen atoms bonded to the same carbon atom, not a hydrogen molecule. Similarly, notation such as $H(OR^5)$ indicates both substituents which are bonded to a carbon having two valences available. Throughout the specification, notation such as $\Delta^N$, e.g. $\Delta^1$, $\Delta^6$ indicates a double bond between two carbon atoms in the cyclopentanophenanthene ring, the superscript number indicating the lowest number ring carbon atom partner to the double bond. These notations are well understood in the art, and are here briefly reviewed for purposes of exemplification.

DETAILED DESCRIPTION OF THE EMBODIMENT

Specific preferred embodiments of this invention may be summarized as follows:

(A) 17α-ethynylprogesterone,
(B) 17α-ethynyl-5α-dihydroprogesterone,
(C) 17α-ethynyl-19-norprogesterone,
(D) 17α-ethynyl-5α-dihydro-19-norprogesterone,
(E) 17α-ethynyl-6α-methylprogesterone,
(F) 17α-ethynyl-6α-methyl-5α-dihydroprogesterone,
(G) 17α-ethynyl-6α-methyl-19-norprogesterone,
(H) 17α-ethynyl-6α-methyl-5α-dihydro-19-norprogesterone,
(I) 17α-ethynyl-6-methylpregna-4,6-diene-3,20-dione,
(J) 17α-ethynyl-6-methyl-19-norpregna-4,6-diene-3,20-dione.

Compounds (C) and (D) respectively represent the 19-nor analogs of compounds (A) and (B), while compounds (E) and (F) represent the 6α-methyl analogs of compounds (A) and (B). Compounds (G) and (H) represent the combination, i.e. the 6-methyl-19-nor derivatives of compounds (A) and (B). Compounds (I) and (J) represent, respectively, the 6-methyl-Δ⁶- and 6-methyl-Δ⁶-19-nor derivatives of compound (A).

The compounds of the present invention have not, according to the inventors' knowledge, hitherto been described in the art. They may be prepared from

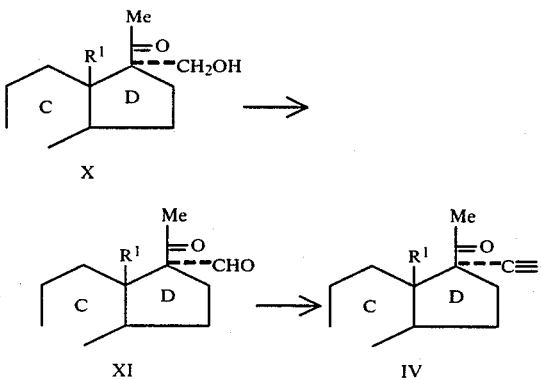

(where $R^1$ is as herein above defined).

17α-Hydroxymethyl-17β-acetyl steroids (X) may be prepared by the method of Mukherjee and Engel (*Steroids*, 34, 597 [1979]; *Can. J. Chem.*, 56, 410 [1978]). Careful oxidation of such hydroxymethyl steroids (X), for example with pyridine chlorochromate in methylene chloride, leads to the hitherto unknown 17α-formyl derivatives (XI). The latter are then converted into the corresponding ethynyl derivative (IV) by treatment with a dialkyl diazomethyl phosphonate in the presence of a deprotonating agent such as, for example, MeLi (Calvin and Hamil, *J. C. S. Perkin Trans.*, 1, 896 [1977]) or potassium tert-butoxide (KOBu$^t$) (Gilbert and Weerasooriya, *J. Org. Chem.*, 47, 1837 [1982]). Dimethyldiazomethyl phosphonate, $N_2CHPO(OMe)_2$ (Seyforth et al., *J. Org. Chem.*, 36, 1379 [1979]) has proved to be particularly suitable for the purpose of this invention. In general terms the reaction is performed by adding ca. one equivalent of dimethyldiazomethylphosphonate in a solvent such as tetrahydrofuran to a slurry of KOBu$^t$ in the same solvent at below ambient temperature and preferably at $-78°$ C., followed by addition of the steroid in the same solvent. The reaction can be monitored by thin layer chromatography. When the reaction is complete, water is added and the organic layer worked up as appropriate.

The reaction may be applied to a wide variety of 17α-formyl steroids containing such groups as:

hydroxyl, for example at $C_1$, $C_2$, $C_3$, $C_4$, $C_5$, $C_6$, $C_7$, $C_{11}$. If acylated, such groups may undergo hydrolysis during the reaction.

alkoxy, aryloxy and aryl, for example, at $C_1$, $C_3$, $C_6$, $C_7$ and $C_{11}$;

oxo, such for example, as oxo at $C_1$, $C_2$, $C_3$, $C_4$, $C_6$, $C_7$ and $C_{11}$;

oxo with conjugated unsaturation such as, for example 3-CO-$\Delta^4$, 3-CO-$\Delta^{4,6}$, 3-CO-$\Delta^{1,4}$, 3-CO-$\Delta^{1,4,6}$, 3-CO-$\Delta^{4,9(10)}$, 3-CO-$\Delta^{4,9(10),11,(12)}$ alkyl such as methyl at $C_1$, $C_2$, $C_3$, $C_4$, $C_5$, $C_6$, $C_7$ and $C_{11}$; 1,2-methylene; 6,7-methylene; 6-methylene; 11-methylene; methylenedioxy, for example, at $C_3$; enol ether, for example, 3-methoxy- and 3-cyclopentyl-3,5-diene;

unsaturated linkages, for example, at $C_1$, $C_2$, $C_3$, $C_4$, $C_{5(10)}$, $C_6$, $C_{9(10)}$, $C_{11(12)}$;

aromatic structures such as 1,3,5(10)estratrienes and derivatives thereof.

Compounds containing moieties (VIII) and (IX) are of particular value because of their binding affinities for the progesterone receptor and potent progestational activity. These compounds include some of the most potent progestational agents known in the art. They may consequently be of value:

in hormone replacement therapy and hormonal imbalance, including menorrhagia, dysmenorrhea, premenstrual syndrome, and for the treatment of hot flushes in menopausal women;

as contraceptives of the "mini-pill" type or long-acting injectables;

for synchronization of estrus in feed lot cattle;

for inhibiting estrus in domestic animals such as the dog or cat;

for treatment of benign prostatic hypertrophy and prostatic cancer;

for treatment of breast and uterine cancer;

as antiandrogens and antiestrogens.

In conjunction with estrogens, and in particular in conjunction with ethynylestradiol, they may be used as the progestagenic component in conventional oral contraceptives and ovulation inhibitors in the various regimens and preparations that are standard in the art.

The compounds of the present invention can be administered in various dosage forms for purposes of oral, parenteral, buccal, nasal, trans-dermal, intrauterine, rectal and vaginal absorption. The active ingredient or ingredients may be enclosed in hard or soft gelatin capsules, or may be compressed directly into tablets. They may be incorporated with pharmaceutical excipients and inert diluents and used in the form of troches, elixirs, suspensions, syrups, wafers, chewing gum and the like. Such compositions and preparations may contain not less than 0.01 mg or more than 1 g of active ingredient per unit dosage form. Preferably an amount of active ingredient ranging from 0.1 mg to 250 mg is employed per unit dosage. The tablets, troches, pills and capsules may also contain pharmaceutical excipients including gum tragacanth, acacia, corn starch, gelatin, a diluent such as dicalcium phosphate, a disintegrating agent such as cornstarch, potato starch, alginic acid, a lubricant such as magnesium stearate, a sweetening agent such as sucrose, lactose, saccharin or aspartame, a flavoring agent such as peppermint oil, oil of wintergreen, or cherry flavoring. Various other materials may also be present as coatings or to otherwise modify the physical form of the dosage unit including shellac coated tablets or capsules and sugar-coated tablets. Syrups and elixirs may contain in addition to steroidal ingredients a sweetening agent such as sucrose, methyl and propyl parabens as preservatives and suitable dyes or flavoring agents.

Parenteral fluid dosage forms or injectable forms including those which may be administered by jet gun may be prepared by utilizing the active ingredient in a sterile liquid vehicle such as water or saline solution. Compositions having the desired clarity, stability and adaptability for parenteral use may be prepared by dissolving from about 0.1 mg to about 3 g of the active ingredient in a vehicle consisting of a mixture of nonvolatile, liquid polyethylene glycols which are soluble in water and organic liquids and have molecular weights ranging from about 200 to about 1,500. These solutions may advantageously contain suspending agents such as sodium carboxymethyl cellulose, methyl cellulose, polyvinyl pyrrolidone or polyvinyl alcohol. Injectable forms may additionally contain preservatives including bactericidal and fungicidal agents such as, for example parabens, pentyl alcohol, phenol or thimerosal. Isotonic agents may be included such as sugars or sodium chloride. Adjuvants such as local anesthetics, stabilizing and buffering agents may also be added.

The active ingredient or ingredients may be compressed into pellets or small cylinders and may be implanted subcutaneously or intramuscularly as depot injections or implants. Implants may employ inert materials such as biodegradable polymers or synthetic silicones including Silastic ®, which is a silicone rubber manufactured by the Dow-Corning Corporation.

When used as a contraceptive, the products of the reaction may be made up in packs standard for such products and well known to those skilled in the art. They may be made up in monthly dosage forms or in an edible matrix which may additionally be dated with days, months or years and with each unit dose readily detachable. Thus, for example, they may be formulated as a strip pack with inclusion of placebo tablets as required. They may also be included as the active steroid in medicated vaginal suppositories or rings or intrauterine devices.

In order to practice the invention, 17β-acetyl-17α-formyl steroids (XI) are required. These compounds are new in the art and, surprisingly, have been found to be stable structures under the experimental conditions of the invention. They may be prepared by careful oxidation of 17β-acetyl-17α-hydroxymethyl steroids (X). The latter are known in the art and have been reported, inter alia, by Mukherjee and Engel, Steroids, 34, 597 (1979); Can. J. Chem, 56, 410 (1978); Wieland, Helv. Chim. Acta, 61, 3068 (1978). No claim is made to these hydroxymethylated steroids. Their oxidation to 17α-formyl steroids may be carried out using mild oxidants such as pyridine/chromic acid, pyridinium chlorochromate, 2,2'-bipyridinium chlorochromate, 2,2'-bipyridine-chromium trioxide complex, RuCl$_2$(PPh$_3$)-benzene, pyridinium chlorochromate on silica gel, chromic acid on silica gel, tetra-n-butylammonium chromate, chromium trioxide-graphite, dimethylsulfoxide activated by electrophiles, μ-oxo-bis(chlorotriphenylbismuth) and the like. Such 17β-acetyl-17α-formyl steroids have not hitherto been described in the art and represent an important new class of steroidal intermediates which fall within the purview of this invention.

Although dimethyldiazomethylphosphonates react with both aldehydes and ketones, selective reaction with one of these moieties in the presence of the other moiety has not yet been established. The inventors have made the surprising discovery that dimethyldiazomethylphosphonate, (preferably present in slight excess over 1 molar equivalent), reacts preferentially with the sterically-hindered formyl group in the presence of, for example, the unhindered 3-CO-Δ$^4$ residue. This is an observation that is important in the art of steroid synthesis.

The products of the invention may be isolated by standard methods used in the art including crystallization, preparative chromotographic techniques, and the like. Such methods are exemplified in the Examples.

SYNTHESIS

The synthetic route to compounds (A) and (B) may be schematically flow charted as follows:

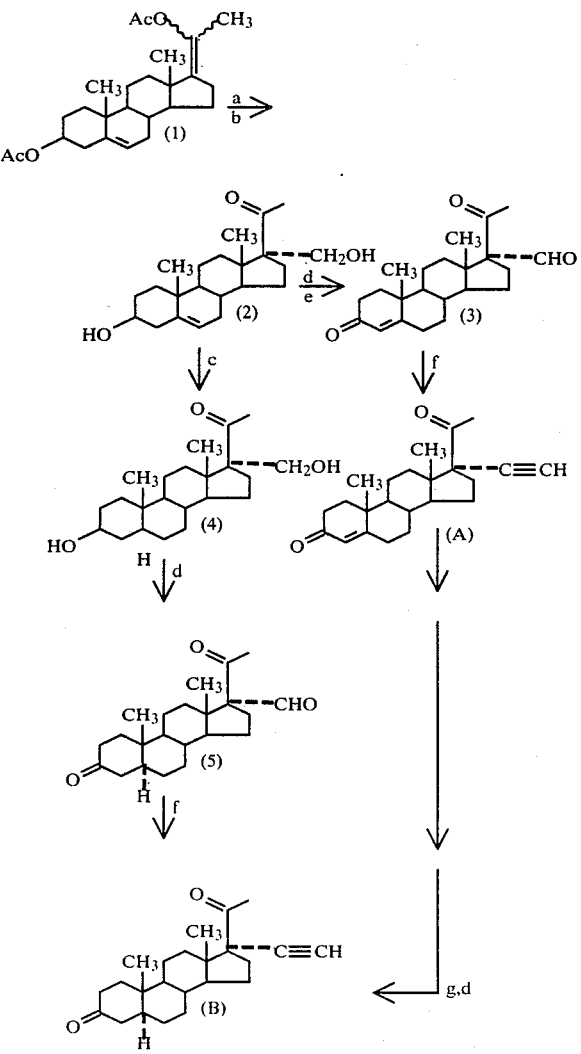

wherein the letters a–g designate the following reagents used to make the indicated conversions:

a. methyl lithium;
b. ZnCl$_2$, CH$_2$O;

c. hydrogenation under an atmosphere of hydrogen using as catalyst palladium on carbon;

d. bipyridinium chlorochromate or pyridinium chlorochromate;

e. acid;

f. O,O-dimethyldiazomethylphosphonate and potassium t-butoxide (N$_2$CHP(O) (OMe)$_2$/KOBu$_t$);

g. lithium/ammonia.

Synthesis of compound (A), 17α-ethynylprogesterone can be effected via the sequence (1)→(2)→(3)→(A) on the flow chart. Conceptually, the synthesis is broken into Examples for the sake of convenience.

1. Synthesis of 17α-formylprogesterone (3) 17α-Hydroxymethyl-3β-hydroxy-5-pregnen-20-one [compound (2), prepared according to D. Mukherjee and C. R. Engel, Steroids 34, 597 (1979)] (5.32 g) was dissolved in hot methylene chloride (2500 mL). Eighteen-hundred mL of the methylene chloride was removed by distillation. Without cooling the concentrated solution was added with mechanical stirring to pyridinium chlorochromate (13.54 g). Distilled H$_2$O (0.5 mL) was added and the mixture was stirred for 1.25 hr at ambient temperature. After filtration through Whatman 1 PS filter paper the filtrate was poured onto a glass column tightly tap-packed with dry thin layer chromatograph grade silica gel adsorbant (750 g) that had been topped with sea sand (1.5 cm). The column was eluted with acetone/methylene chloride (2.5:97.5, v/v). Fractions containing the product (17α-formylpregn-5-ene-3,20-dione) were combined and evaporated. The residue was dissolved in a mixture of methylene chloride (20 mL), methanol (80 mL) and 10% aqueous hydrochloride acid (20 mL) and kept for 3 hr at ambient temperature. Partition between methylene chloride and distilled H$_2$O and evaporation of the methylene chloride left a residue of 17α-formylprogesterone which was used without further purification. The compound exhibited $^1$H-NMR peaks at δ0.82 (18-CH$_3$), 1.13 (19-CH$_3$), 2.18 (21-CH$_3$), 5.68 (4-H) and 9.80 (H—C=O) ppm and a molecular ion at a mass m/e 342.

2. Synthesis of 17α-Ethynylprogesterone (A) 17α-Formylprogesterone (compound (3), 7.1 g), was allowed to react with a mixture of O,O-dimethyl diazomethylphosphonate [prepared according to Seyferth et al., J. Org. Chem. 36, 1348 (1971) and Gilbert and Weerassooruja, J. Org. Chem. 44, 4997 (1979), 3.38 g] and potassium t-butoxide (2.53 g) in tetrahydrofuran (145 ml) at −78° C. for 15.5 hr under an anhydrous nitrogen atmosphere and then warmed to room temperature. The product was obtained by dilution was distilled H$_2$O and extraction with methylene chloride followed by chromatography on a dry silica gel column eluted with acetone/methylene chloride (2.5:97.5, v/v). Pure 17α-ethynylprogesterone was obtained by evaporation of the appropriate fractions and crystallizations first from methanol and finally acetonitrile. The melting point was around 179°–81° C. The compound exhibited $^1$H-NMR peaks at 0.63 (18-CH$_3$), 1.17 (19-CH$_3$), 2.28 (21-CH$_3$), 2.42 (—C≡C—H) and 5.72 (4-H) ppm and showed a molecular ion in its high resolution mass spectrum at m/e 338.2245 (calcd. 338.2245).

The synthesis of 17α-ethynyl-5α-dihydroprogesterone (compound (B)), i.e. (1)→(2)→(4)→(5)→(B) as per the flow chart, may be described by the synthesis following, which synthesis is again broken into Examples as illustrated by the flow chart for conceptual ease, starting with the synthesis of 17α-hydroxymethyl-3β-hydroxy-5α-pregnan-20-one (compound (4)) from 17α-hydroxymethyl-3β-hydroxy-5-pregnen-20-one (compound (2), described above).

3. Synthesis of 17α-hydroxymethyl-3β-hydroxy-5α-pregnan-20-one (4)—To 155 mg of 17α-hydroxymethyl-3β-hydroxypregn-5-en-20-one (compound (2)) in 20 ml of ethanol was added 50 mg of 10% palladium on charcoal catalyst and the mixture was hydrogenated under one atmosphere of hydrogen for 15 hr at ambient temperature. Filtration removed the catalyst and evaporation of solvent left a residue consisting of 17α-hydroxymethyl-3β-hydroxy-5α-pregnan-20-one (4). This compound may be recrystallized from methylene chloride/methanol and had a melting point of 213°–215° C. The $^1$H-NMR spectrum exhibited peaks at δ0.63 (18-CH$_3$), 0.80 (19-CH$_3$), 2.18 (21-CH$_3$) and 3.4–4.4 (17α-CH$_2$—OH and 3α-H) ppm.

4. Synthesis of 17α-Formyl-5α-pregnane-3,20-dione (5)—A solution of 17α-hydroxymethyl-3β-hydroxy-5α-pregnan-20-one (compound (4), 130 mg)) in methylene chloride (25 ml) was stirred with pyridinium chlorochromate (150 mg) at ambient temperature for 3 hr. The reaction mixture was extracted with methylene chloride, and the product, 17α-formyl-5α-pregnane-3,20-dione (compound (5)) was further purified by SiO$_2$ column chromatography employing acetone/methylene chloride (5:95, v:v) as the solvent system.

5. Synthesis of 17α-Ethynyl-5α-pregnane-3,20-dione (B)—17α-Formyl-5α-pregnane-3,20-dione (compound (5), 94.6 mg), O,O-dimethyl diazomethylphosphonate (54 mg) and potassium t-butoxide (36 mg) were allowed to react in tetrahydrofuran (5.0 ml) as described in Example 2 above. Reaction workup as described for 17α-ethynyl-progesterone yields 17α-ethynyl-5α-pregnane-3,20-dione, which may be recrystallized from methanol. The product had a melting point of 174°–175° C., $^1$H-NMR peaks at δ0.64 (18-CH$_3$), 1.00 (19-CH$_3$), 2.28 (21-CH$_3$), 2.42 (C≡CH) ppm and a molecular ion in the mass spectrum at m/e 340.

Compound (B) may also be prepared directly from compound (A) based on the well-known Li/NH$_3$ reduction of steroidal Δ$^4$-3-ketones. This synthesis route is, however, less preferred than the above procedure since a complex mixture is generally obtained due to co-reduction of the C-20 ketone and ethynyl groups which yields, respectively, the 20-hydroxy-17-ethynyl derivative as the major product together with a substantial amount of the 17-vinyl derivative. The mixture may, however, be chromatographically separated.

The following three examples (6–8) together provide for synthesizing the 6α-methyl and 6-methyl-Δ$^6$ analogs of 17α-ethynylprogesterone (A).

6. Synthesis of 17α-Formyl-6α-methylprogesterone—17α-hydroxymethyl-3β-hydroxy-6-methyl-pregn-5-en-20-one was prepared from 3β-acetoxy-6-methylpregn-5-en-20-one by a procedure analogous to the one used for the preparation of 17α-Hydroxymethyl-3β-hydroxy-5-pregnen-20-one (cf. Example 1). It had a melting point of about 219°–235° C., exhibited $^1$H-NMR peaks (CDCl$_3$:CD$_3$OD, 1:1, v:v) at 0.67 (18-CH$_3$), 1.00 (19-CH$_3$), 1.62 (6-CH$_3$), 2.20 (21-CH$_3$), 3.35 (3-H, m), 3.57 and 4.17 (CH$_2$—OH, two doublets, J=10 Hz) and a molecular ion at m/e 360.2666 (C$_{23}$H$_{36}$O$_3$ requires 360.2664). Oxidation, isomerization and purification according to the method of Example 1 yielded 17α-formyl-6α-methylprogesterone. It exhibited $^1$H-NMR peaks at 0.83 (18-CH$_3$), 1.13 (19-CH$_3$), 1.05 (6α-CH$_3$, d, J=6 Hz), 2.18 (21-CH$_3$), 5.70 (4-H, d, J=1–2

Hz) and 9.77 (H—C=O) ppm and a molecular ion at m/e 356.2352 ($C_{23}H_{32}O_3$ requires 356.2351).

7. Synthesis of 17α-Ethynyl-6α-methylprogesterone—By the method of Example 2, 17α-formyl-6α-methylprogesterone was converted into 17α-ethynyl-6α-methylprogesterone. This compound melted around 200°–202° C. It exhibited $^1$H-NMR peaks (CDCl$_3$) at 1.05 (18-CH$_3$), 1.13 (19-CH$_3$), 1.02 (doublet, 6α-CH$_3$), 2.32 (21-CH$_3$), 2.38 (—C≡C—H) and 5.68 (4-H, d, J=1 Hz) ppm and showed a molecular ion at m/e 352.2406 ($C_{24}H_{32}O_2$ requires 352.2401).

8. Synthesis of 17α-Ethynyl-6-methylpregna-4,6-diene-3,20-dione (6-methyl-6-dehydroprogesterone)—17α-Ethynyl-6α-methylprogesterone (40 mg), p-toluenesulfonic acid (2 mg) and chloranil (40 mg) were allowed to react in xylene (5 ml) for 1 hr at reflux. The resulting mixture was diluted with ethyl acetate and shaken with 1% sodium hydroxide and the organic layer evaporated at reduced pressure. The product was obtained by chromatography on a silica gel column eluted with ethyl acetate/hexanes (1:3, v/v). Pure 17α-ethynyl-6-methylpregna-4,6-diene-3,20-dione was obtained by evaporation of the appropriate fractions and crystallization of the residue from ethyl acetate. It melted around 234°–236° C., exhibited $^1$H-NMR peaks at 0.70 (18-CH$_3$), 1.07 (19-CH$_3$), 1.83 (6-CH$_3$), 2.30 (21-CH$_3$) 2.43 (—C≡C—H), 5.82 (4-H) and 5.90 (7-H) ppm and showed a molecular ion in its mass spectrum at m/z 350.2243 (calcd. 350.2245).

9. Synthesis of 3-Methoxy-17α-ethynyl-19-norpregna-1,3,5(10)-triene—Crude 3-methoxy-19-norpregna-1,3,5(10)-trien-20-ol [0.95 g, prepared according to A. Kruber and E. Olivetto, J. Org. Chem. 31, 24 (1965)] in methylene chloride (100 mL) was stirred with pyridinium chlorochromate (0.9 g) at room temperature for 5 hours. The crude reaction mixture was transferred directly onto a dry silica gel column and eluted with CH$_2$Cl$_2$ to give 3-methoxy-19-norpregna-1,3,5(10)-trien-20-one which exhibited $^1$H-NMR peaks at δ0.98 (18-CH$_3$), 2.15 (21-CH$_3$) and 3.8 (O—CH$_3$), and an IR absorption band in CHCl$_3$ at 1705 cm$^{-1}$ (20—C=O). This compound was converted to 3-methoxy-17α-hydroxymethyl-19-norpregna-1,3,5(10)-triene by the procedure used to convert 3β-hydroxy-5-pregnen-20-one to its 17α-hydroxymethyl analog (cf. the procedure of Mukherjee and Engle quoted in Example 1). The crude product was purified by silica gel dry column chromatography employing 5% acetone in CH$_2$Cl$_2$ as solvent system to provide the desired 17α-hydroxymethyl derivative. It exhibited $^1$H-NMR peaks at δ0.70 (18-CH$_3$), 2.20 (21-CH$_3$), 3.76 (OCH$_3$), and doublet peaks centered at 3.70 and 4.20 (17α-CH$_2$) and IR bands at 3400 (OH) and 1705 (20—C=O) cm$^{-1}$ in CHCl$_3$.

The latter compound (310 mg) in 50 mL of CH$_2$Cl$_2$ was stirred with 250 mg of pyridinium chlorochromate at room temperature for 18 hours. The mixture was poured directly onto a dry silica gel column and eluted with 5% acetone in methylene chloride. The major column fraction contained 17α-formyl-3-methoxy-19-norpregna-1,3,5(10)-trien-20-one which exhibited $^1$H-NMR peaks at δ0.80 (18-CH$_3$), 2.20 (21-CH$_3$), 3.75 (OCH$_3$) and 9.87 (—CHO) and IR bands at 1720 (CHO) and 1692 (C=O) cm$^{-1}$ in CHCl$_3$. This last compound was converted by the procedure of Example 2 to 3-methoxy-17α-ethynyl-19-norpregna-1,3,5(10)-triene, which was purified by silica gel column chromatography and recrystallization from methanol. It melted around 123°–124° C., showed a molecular ion in its high resolution mass spectrum at m/e 336.2087 (calcd for $C_{23}H_{28}O_2$, 336.2088), exhibited $^1$H-NMR peaks at δ0.60 (18-CH$_3$), 2.28 (21-CH$_3$), 2.48 (—C≡CH) and 3.74 (O—CH$_3$), and IR bands at 3305 (C≡C—H) and 1700 (C=O) cm$^{-1}$.

10. Synthesis of 17α-ethynyl-19-nor-4-pregnene-3,20-dione—The reaction of 17α-hydroxymethyl-3-methoxypregna-1,3,5(10)-trien-20-one (prepared as in Example 9) (0.98 g) in 15 mL each of tert-butanol and tetrahydrofuran with lithium (0.8 g) in ammonia (60 mL) at −78° C. was quenched with saturated ammonium chloride solution (5 mL) after 3.5 hours. Excess ammonia was evaporated under a slow stream of nitrogen. The white residue was diluted with water and partitioned between ethyl acetate and aqueous phase. The combined organic extracts were dried and concentrated to give crude reaction product which was dissolved in methanol (50 mL) and treated with 10% (v/v) HCl solution (10 mL). The mixture was stirred at 50° C. for 1 hour. Methanol was evaporated and the residue was diluted with water. The product was extracted with ethyl acetate three times. The combined organic extracts were dried over sodium sulfate, filtered and concentrated. Silica gel column chromatography of the crude reaction product, employing 5% acetone in CH$_2$Cl$_2$ as solvent system, provided 17α-hydroxymethyl-20-hydroxy-19-nor-4-pregnen-3-one as the major product. It exhibited $^1$H-NMR peaks at δ0.80 (18-CH$_3$), 1.32 (doublet, 21-CH$_3$), 3.5–4.2 (17-CH$_2$OH) and 5.75 (4-H). Oxidation according to the procedure of Example 1 yielded 17α-formyl-19-nor-4-pregnene-3,20-dione which was purified by silica gel column chromatography employing CH$_2$Cl$_2$ as eluting solvent. It exhibited $^1$H-NMR peaks at δ0.85 (18-CH$_3$), 2.20 (21-CH$_3$), 5.73 (4-H) and 9.80 (—CHO) and IR bands at 1720 (CHO), 1710 (C=O) and 1670 (enone) cm$^{-1}$. This compound was converted by the procedure of Example 2 to 17α-ethynyl-19-nor-4-pregnene-3,20-dione, which was purified by silica gel column chromatogrphy employing 3% acetone in CH$_2$Cl$_2$ and repeated recrystallization from methanol. The compound melted around 128°–129° C. It showed a molecular ion in its high resolution mass spectrum at m/e 324.2088 (calcd for $C_{22}H_{28}O_2$, 324.2099), IR bands at 3302 (—C≡C—H), 1705 (20—C=O) and 1680 (3-enone) cm$^{-1}$ and $^1$H-NMR peaks at δ0.68 (18-CH$_3$), 2.28 (21-CH$_3$), 2.40 (—C≡CH) and 5.80 (4-H).

11. Synthesis of 17α-Ethynyl-19-nor-5α-pregnane-3,20-dione—To liquid ammonia (25 mL) containing lithium wire (10 mg) was added 17α-hydroxymethyl-20-hydroxy-19-nor-4-pregnen-3-one (prepared as in Example 10) (130 mg) in 1.5 mL each of dioxane and ether and the mixture was stirred at −78° C. for 2 hours. The reaction was quenched by addition of 2 mL of saturated ammonium chloride solution. Workup as above gave a crude reaction product which was dissolved in CH$_2$Cl$_2$ (50 mL) and treated with pyridinium chlorochromate (120 mg). The mixture was stirred at ambient temperature for 3 hours. The reaction mixture was filtered through a short celite column and the filtrate and methylene chloride washings were combined and concentrated. The residue obtained was purified by silica gel column chromatography, employing CH$_2$Cl$_2$ as the eluting solvent to afford 17α-formyl-19-nor-5α-pregnane-3,20-dione. It showed a molecular ion in its high resolution mass spectrum at m/e 330.2196 (calcd for $C_{21}H_{30}O_3$, 330.2195) and $^1$H-NMR peaks at δ0.82 (18-CH$_3$), 2.20 (21-CH$_3$) and 9.82 (—CHO). This compound was converted according to the procedure of Example 2 to 17α-ethynyl-19-nor-5α-pregnane-3,20-dione which was purified by silica gel column chromatography. This compound showed a molecular ion in its high resolution mass spectrum at m/e 326.2244 (calcd for $C_{22}H_{30}O_2$, 326.2245), IR bands at 3302 (C≡C—H) and 1708 (3,20 C=O) cm$^{-1}$ and $^1$H-NMR peaks at δ0.62 (18-CH$_3$), 2.29 (21-CH$_3$) and 2.42 (s, 1, —C≡CH).

Progesterone and Androgen Receptor Binding

The in vitro biological activity of the 17α-ethynyl-progesterone series and several known progestagens were determined by measuring the binding affinities (RBA) of these compounds relative to progesterone for the cytosol progesterone receptor of the estrogen-primed immature rabbit uterus. The results are summarized in Table 1.

TABLE 1

Relative Binding Affinities (RBA) of a Series of 17α-Ethynylprogesterones and Other Known Progestagens for the Cytosol Progesterone Receptor of the Estrogen-primed Immature Rabbit Uterus, 16–18 Hour Incubation Period

| COMPOUND | RBA (%) |
|---|---|
| Assay 1 | |
| Progesterone | 100 |
| 17α-Ethynylprogesterone | 156 |
| 5α-Dihydro-17α-ethynylprogesterone (lot 1) | 11 |
| Levonorgestrel | 111 |
| Assay 2 | |
| Progesterone | 100 |
| 17α-Ethynylprogesterone | 267 |
| 5α-Dihydro-17α-ethynylprogesterone (lot 1) | 186 |
| 5α-Dihydro-17α-vinylprogesterone | 47 |
| Assay 3 | |
| Progesterone | 100 |
| 17α-Ethynylprogesterone | 144 |
| 5α-Dihydro-17α-ethynylprogesterone (lot 1) | 144 |
| 5α-Dihydro-17α-ethynylprogesterone (lot 2) | 133 |
| 5α-Dihydro-17α-vinylprogesterone | 51 |
| Assay 4 | |
| Progesterone | 100 |
| 17α-Ethynyl-19-norprogesterone | 100 |
| 5α-Dihydro-17α-ethynyl-19-norprogesterone | 67 |
| 6α-Methyl-17α-ethynylprogesterone | 63 |
| 6α-Methyl-17α-acetylpregn-4-ene-20-yn-3-one | 5 |
| 6α-Methyl-17α-acetoxyprogesterone (Provera ®) | 57 |
| 6α-Methylprogesterone | 57 |
| Assay 5 | |
| Progesterone | 100 |
| 17α-Ethynyl-19-norprogesterone | 133 |
| 5α-Dihydro-17α-ethynyl-19-norprogesterone | 66 |
| 6α-Methyl-17α-ethynylprogesterone | 67 |
| 6α-Methyl-17α-acetylpregn-4-ene-20-yn-3-one | 6 |
| 6α-Methyl-17α-acetoxyprogesterone (Provera ®) | 133 |
| 17α-Acetoxyprogesterone (Prodox ®) | 122 |
| Assay 6 | |
| Progesterone | 100 |
| 6α-Methyl-17α-ethynylprogesterone | 91 |
| 6-Methyl-6-dehydro-17α-ethynylprogesterone | 104 |
| 6α-Methyl-17α-acetoxyprogesterone (Provera ®) | 143 |
| 17α-Acetoxyprogesterone (Prodox ®) | 114 |

The data in Table 1 indicate that, in general, compounds of the 17α-ethynylprogesterone series bind more avidly to the progesterone receptor than does progesterone. 17α-ethynylprogesterone displayed a relative binding affinity (RBA) for the rabbit uterine progesterone receptor of 189±55 (X±S.D.) as determined in three assays using the standard 16 to 18 hour incubation period at 0° C. The 5α-reduced analog of 17α-ethynylprogesterone also exhibited high binding affinity, with an RBA of 154±23. One spurious result (RBA=11) was not included in the average inasmuch as the inventors believed it to be flawed. That is, the binding of labeled progesterone was very low, making the results of displacement questionable (i.e., probably little receptor was present). Thus, 5α-reduction of 17α-ethnylprogesterone has negligible effects on the binding affinity for the progesterone receptor.

5α-Dihydro-17α-vinylprogesterone was obtained as an over-reduced byproduct in the preparation of 5α-dihydro-17α-ethynlprogesterone from 17α-ethynylprogesterone. The RBA of this compound relative to the two 17α-ethynylated progesterones was substantially lower (RBA=47, 51), indicating the importance of the 17α-ethynyl group for avid binding to the progesterone receptor (Table 1).

In two separate assays, 17α-ethynyl-19-norprogesterone had RBA's for the progesterone receptor of 100 and 133, respectively (Table 1). Hence, deletion of the 10β-methyl group of 17α-ethynylprogesterone did not enhance progesterone receptor affinity in a manner analogous to that for the progesterone, that is, 19-norprogesterone had an RBA of 258 relative to an RBA of 100 for progesterone (Kontula et al., Acta Endocrinal. 78, 574, 1975). Nonetheless, the progesterone receptor binding affinity of 17α-ethynyl-19-norprogesterone was still slightly greater than that of progesterone itself.

The correspnding 5α-reduced compound, 5α-dihydro-17α-ethynyl-19-norprogesterone, displayed RBA's of 66 and 67 in two separate assays, implying that in the 19-nor series unsaturation of C-4 makes a significant contribution to progesterone receptor binding affinity (Table 1).

The 6α-methyl or 6-methyl-6-dehydro derivaties of 17α-acetoxy-progesterone (i.e., Provera ® and Megestrol Acetate) are known to be potent orally active progestational compounds. Therefore, the 6α-methyl and 6α-methyl-6-dehydro derivatives of 17α-ethynylprogesterone were prepared and their binding affinity for the progesterone receptor determined. In two separate assays, 6α-methyl-17α-ethynylprogesterone had RBA's of 67 and 91, respectively. Further, 6α-methyl-6-dehydro-17α-ethynyl-progesterone displayed an RBA of 104 for the progesterone receptor (Table 1). In contrast, the C-17 stereoisomer of 6α-methyl-17α-ethynyl-progesterone possessed greatly reduced binding affinity for the progesterone receptor (RBA's of 5 and 6), indicating that the 17α-ethynyl-17β-acetyl stereochemical configuration is crucial for progesterone receptor binding in this series.

The inventors additionally determined, in comparison with the Table 1 data for incubation periods of 16–18 hours for 17α-ethynylprogesterone and the 5α-dihydro analog, respectively, that the RBA's were 352 and 211 when assayed in a two-hour incubation at 0° C. The significance of this stems from the work of Bouton and Raynaud (J. Steroid Biochem. 9, 9, 1978 and Endocrinology 105, 509, 1979) and Bouton et al., J. Steroid Biochem. 9, 836 (1978) who established that the measurement of RBA's under different incubation conditions, chosen in relation to the kinetics of the interaction between the natural hormone and its cytoplasmic receptor, can constitute an in vitro assay to screen for steroid hormone agonists and antagonists. RBA values recorded at 0° C. after short incubation times (e.g., 2 hr) mainly reflect differences in the association rate constants of the competing ligands, whereas those measured after long incubation times (e.g., 16 to 24 hr) and/or higher temperatures predominantly are influenced by differences in the dissociation rate constants of the competing ligands. RBA's determined after short incubation times primarily reflect the association of the competitor compared to the natural hormone. Conversely, RBA's measured after long incubation times reflect the dissociation rate of the competitor compared to the natural hormone. Since 17α-ethynylprogesterone and the 5α-dihydro analog exhibited RBA's exceeding 100 for both the short and long-term incubations, it is likely that these compounds have a higher association rate constant and a lower dissociation rate constant than progesterone. Characteristics such as these are highly desirable for a potent progestational agent.

The assay which measures RBA is wellknown to the art and essentially amounts to a competitive binding assay wherein radiolabeled progesterone is used as one of the competing ligands for the rabbit uterine progesterone receptor. The binding affinity of any other ligand (which is, of course, non-radioactive) can then be measured by allowing a known amount of that ligand plus radiolabeled progesterone to compete for a limited number of binding sites. The assay components are combined, allowed to equilibrate, and unbound radioactivity removed by charcoal adsorption. The radioactivity counted in the remaining sample supernatant is a direct measure of bound progesterone and, therefore, is a direct measure of bound competing ligand and its associated relative (to progesterone) binding affinity. For specific details of the assay one may consult, for example, Reel et al, Fertility and Sterility, 31, 552, (1979). The specific conditions and reagents used to determine the RBA's shown in Table 1 are as follows:

Animal species. Immature female New Zealand White rabbits weighing 0.8 to 1.0 kg (Dutchland Laboratories, Inc., Denver, Pa).

Pretreatment. Subcutaneous treatment with 15 μg 17β-estradiol/0.6 ml sesame oil each morning (0830 to 0930 hr) for three days. Animals sacrificed 24 hr after final injection.

Tissue. Uterus; each uterus weighed about 1.0 g and two or three uteri were pooled for each assay.

Dilution Factor: 1:8.

Buffer. (A) 0.01M TES, pH 7.4, 1 mM EDTA, 0.012M thioglycerol and 30% glycerol for cytosol preparation and $^3$H-steroid, unlabeled hormone and compound solutions. (B) 0.01M TES, pH 7.4, 1 mM EDTA and 0.012M thioglycerol for charcoal solution.

Homogenization. Five or six 5-second bursts with 30 second cooling periods between bursts using Brinkman Polytron Pt. 10 at 3.5 rheostat setting.

Temperature. 0°–4° C. for all steps.

Centrifugation. 45,000 rpm for 1 hr, 50 Ti rotor, Beckman L8-80 ultracentrifuge.

Radiolabel. [1,2,6,7-$^3$H(N)]progesterone-22,000 cpm/0.1 ml.

Amount of Addition. 0.1 ml cytosol, 0.1 ml $^3$H-progesterone, 0.1 ml test drug, 0.3 ml buffer.

Incubation. 16–18 hr at 4°–6° C.

Concentrations. $1 \times 10^{-10}$M to $1 \times 10^{-5}$M (7 concentrations).

Method. Charcoal adsorption method used to remove unbound radioactivity. Five-tenths ml of dextran-coated charcoal (0.5% Norit A and 0.05% dextran T-70) added to all tubes except total radioactivity tubes (0.5 ml buffer [B] added), tubes vortexed 3–5 sec, allowed to sit for 10 minutes and centrifuged 10 minutes at 2000 rpm in Beckman TJ-6 centrifuge at 0°–4° C. Supernatant fraction (0.6 ml) decanted into 10 ml of scintillation fluid and counted in Packard Liquid Scintillation Spectrometer 3255 for 1 minute after 20 minute cooling period.

Data Interpretation. Competitive binding curves are generated by plotting the percentage of bound [$^3$H]progesterone versus the concentration of the competitor. The relative binding affinity (RBA) of each compound was calculated by using the following equation.

$$RBA = \frac{[P]_{50\%}}{[C]_{50\%}} \times 100$$

where $[P]_{50\%}$ = molar concentration of unlabeled progesterone required to decrease bound [$^3$H]progesterone to 50% of the buffer control (100% bound [$^3$H]progesterone)

$[C]_{50\%}$ = molar concentration of test compound required to decrease bound [$^3$H] progesterone to 50% of the buffer control (100% bound [$^3$H]progesterone).

Additionally, although the progesterone receptor binding affinity of 17α-ethynylprogesterone (A) is high, it exhibits little if any androgenic side effects inasmuch as the compound has an extremely low binding affinity for male rat androgenic receptors, as shown by the data of Table 2.

TABLE 2

Relative Binding Affinity of 17α-Ethynyl-progesterone for the Cytosol Androgen Receptor of the Castrate Adult Rat Ventral Prostate

| COMPOUND | RBA (%) |
|---|---|
| 5α-Dihydrotestosterone | 100 |
| 17α-Ethynylprogesterne | 0.09 |

The assay used to measure the RBA for the androgen receptor and, by inference, androgenic activity, is analogous to the assay used for measuring progesterone receptor binding affinity except that the binding sites are androgenic rather than progesterone receptors. The assay is well known and widely described, see, for example, Cunningham et al., Steroids, 33, 261 (1979); Wright et al., J. Steroid Chem. 10, 419 (1979); and Toth et al., J. Steroid Biochem. 17, 653 (1982). The specific conditions, reagents, etc. used to derive the data from Table 2 are as follows:

Animal Species. Adult male rat (Charles River CD).

Pretreatment. Castration 17-24 hour prior to sacrifice.

Tissue. Ventral prostate. Amount of tissue: 0.4 g/rat. Several ventral prostate glands pooled for each assay.

Dilution Factor. 1:1.

Buffer. 0.05M Tris HCl, 0.05M Trisbase; 1 mM EDTA; 0.15 mM Dithiothreitol. Solution made of 2.32 mg DDT/ml distilled $H_2O$ (15 mM) so that 10 l of solution added per ml cytosol yields a final concentration of 0.15 mM. Solution prepared fresh daily and added to cytosol after sample taken for protein analysis.

Homogenization. Three five-second bursts with 30 second cooling periods between bursts using Brinkman Polytron Pt. 10 (3.5 setting).

Temperature. 0°–4° C. all steps.

Centrifugation. 45,000 rpm for 1 hr, 50 Ti rotor, Beckman L8-80 ultracentrifuge.

Radiolabel. 1,2-$^3$H-Dihydrotesterone-25,00 cpm/0.1 ml.

Amounts of Addition. 0.1 ml cytosol, 0.1 ml $^3$H-dihydrotestosterone, 0.1 ml test compound, 0.3 ml buffer.

Incubation. 16-18 hours at 0°–4° C.

Concentrations. $1 \times 10^{-10}$M to $1 \times 10^{-5}$ (7 concentrations).

Method. Charcoal adsorption method used to remove unbound radioactivity. Five-tenths ml dextran-coated charcoal (0.5% Norit A and 0.05% dextran T-70) added to all except total radioactivity tubes (0.5 ml buffer added), tubes vortexed 35 seconds, allowed to sit 10 min and centrifuged 10 min at 2000 rpm in Beckman TJ-6 centrifuge at 0°–4° C. Supernatant decanted into 10 ml scintillation fluid and counted in Packard Liquid Scintillation Spectrometer 3255 for 1 min after 20 min cooling period.

Interpretation. The relative binding affinity (RBA) of each compound was calculated as described above for the progesterone receptor binding assay.

Progestational Activity

17α-Ethynylprogesterone (A) and 17α-ethynyl-5α-dihydroprogesterone (B) were tested for progestational activty using the Clauberg assay (Clauberg, Zentr. Gynakol. 54, 2757 1930) as modified by McPhail, J. Physiol. (London) 83, 145 (1935). Immature New Zealand White rabbits weighing 0.8 to 1.0 kg were injected subcutaneously (sc) with 5 µg estrone in 0.5 ml peanut oil on days 1, 3, and 5. On days 7, 8, 9 and 10 the rabbits were treated sc or orally with 0.5 ml peanut oil (control), progesterone or test compound. The animals were sacrificed one day after the final injection (day 11) and the uteri removed and weighed. A 5 cm central segment of each uterine horn was excised and immersion-fixed in neutral-buffered 10% formalin. The fixed uterine segments were trimmed, processed, embedded and sectioned at 6 microns. After staining, the degree of endometrial arborization was scored under a stereomicroscope using the McPhail Index (0-4). A rating of 0 indicated a complete lack of endometrial arborization (no progestational activity), 1 through 3 progressive degrees of activity, and 4 a maximal response.

The in vivo progestational activity (as opposed to in vitro data like that shown in Tables 1 and 2) of 17α-ethynylprogesterone administered subcutaneously compares very favorably with that for progesterone per se, as shown by the data in Tables 3 and 4. Importantly, it should be noted that subcutaneously administered 17α-ethynylprogesterone achieves substantially the same or greater effect as subcutaneously administered progesterone, as revealed by an examination of uterine weight and McPhail index, but at approximately one-tenth to one twentieth the dosage level, indicating 10 to 20 times greater potency for subcutaneous administration.

Significantly, Table 3 shows a comparison between orally administered 17α-ethynylprogesterone and subcutaneously (sc) administered progesterone, and indicates that, for equivalent levels, oral 17α-ethynylprogesterone possesses progestational activity equivalent to subcutaneous progesterone.

In the initial bioassay, 17α-ethynylprogesterone was tested at sc doses of 50, 100, 200 and 400 µg/rabbit/day. All four doses induced full progestational responses (Table 4). In order to establish a dose-response relationship, 17α-ethynylprogesterone was evaluated at four lower sc doses. The compound proved inactive at 2.5 µg/rabbit/day, but doubling of this dose resulted in a partial progestational response. Subcutaneous doses of 10 and 20 µg/rabbit/day stimulated maximal progestational responses (Table 3). Testing of graded sc doses of progesterone in the same assay allowed a determination of the potency of 17α-ethynylprogesterone relative to progesterone. From a plot of the McPhail rating versus the $\log_{10}$ dose, it was estimated that 17α-ethynylprogesterone had a progestational potency 13 times greater than progesterone when administered by the sc route.

TABLE 3

Progestational Activity of 17α-Ethynylprogesterone in the Clauberg Assay*

| Compound | Daily Dose** (µg/rabbit) | Uterine Weight (g) (X ± S.D.) | McPhail Index (0-4) (X ± S.D.) |
|---|---|---|---|
| Control (sc) | 0.5 ml peanut oil | 1.51 ± 0.75 | 0.08 ± 0.11 |
| Progesterone (sc) | 50.0 | 1.09 ± 0.09 | 0.85 ± 0.41 |
|  | 100.0 | 1.64 ± 0.23 | 2.90 ± 0.28 |
|  | 200.0 | 2.83 ± 0.26 | 3.97 ± 0.05 |
| 17α-Ethynyl-progesterone (sc) | 2.5 | 0.90 ± 0.06 | 0.17 ± 0.23 |
|  | 5.0 | 1.63 ± 0.45 | 1.50 ± 0.54 |
|  | 10.0 | 3.23 ± 0.83 | 3.83 ± 0.12 |
|  | 20.0 | 4.41 ± 0.33 | 4.00 ± 0.00 |
| 17α-Ethynyl-progesterone (orally) | 10.0 | 0.94 ± 0.09 | 0.08 ± 0.11 |
|  | 20.0 | 0.98 ± 0.18 | 0.04 ± 0.06 |
|  | 50.0 | 0.86 ± 0.02 | 0.00 ± 0.00 |
|  | 100.0 | 1.79 ± 0.63 | 1.38 ± 1.46 |

*This assay employs estrone-primed immature New Zealand White rabbits. For methods refer to Reel et al, Fertility and Sterility 31, 552 (1979).
**This assay utilized three rabbits per dose group. Peanut oil or compound was administered by the route indicated.

TABLE 4

Progestational Activity of 17α-Ethynylprogesterone in the Clauberg Assay*

| Compound | Daily Dose** (µg/rabbit) | Uterine Weight (g) (X ± S.D.) | McPhail Index (0-4) (X ± S.D.) |
|---|---|---|---|
| Control (sc) | 0.5 ml peanut oil | 0.62 ± 0.10 | 0 ± 0.00 |
| Progesterone (sc) | 200 | 3.93 ± 1.32 | 3.96 ± 0.06 |
| 17α-Ethynyl-progesterone (sc) | 50 | 5.54 ± 0.18 | 4.0 ± 0.00 |
|  | 100 | 4.19 ± 0.22 | 4.0 ± 0.00 |
|  | 200 | 4.99 ± 0.89 | 4.0 ± 0.00 |
|  | 400 | 5.90 ± 1.75 | 4.0 ± 0.00 |

*This assay employs estrone-primed immature New Zealand White rabbits. For methods refer to Reel et al, Fertility and Sterility 31, 552 (1979).
**This assay utilized three rabbits per dose group. The peanut oil and compound were administered by the subcutaneous (sc) route.

In order to obtain more information concerning the oral progestational activity of 17α-ethynylprogesterone, this compound was tested at higher doses in a further assay. In contrast to the first assay (Table 3), 17α-ethynylprogesterone was inactive at an oral doses of 100 μg/rabbit/day (Table 5). This observation suggests that this quantity of the compound is near the oral threshold dose. Oral doses of 200 and 400 μg 17α-ethynylprogesterone/rabbit/day stimulated partial progestational responses (Table 5).

5α-Dihydro-17α-ethynylprogesterone was evaluated in the Clauberg Assay at sc doses of 5, 10, 20, 100, 200 and 400 μg/rabbit/day and at oral doses of 100, 200 and 400 μg/rabbit/day (Tables 6 and 7). This compound proved inactive at all doses examined, whether given subcutaneously or orally.

17α-Ethynyl-19-norprogesterone was evaluated in the Clauberg Assay at sc doses of 2.5, 5, 10 and 20 μg/rabbit/day and at oral doses of 50, 100, 200 and 400 μg/rabbit/day (Tables 7 and 8). By the sc route 17α-ethynyl-19-norprogesterone was about 100 times more potent than progesterone. In contrast, when given by the oral route, 17α-ethynyl-19-nor-progesterone had a potency roughly comparable to subcutaneously administered progesterone (Tables 7 and 8).

6α-Methyl-17α-ethynylprogesterone was tested in the Clauberg Assay at sc doses of 2.5, 5, 10, and 20 μg/rabbit/day and at oral doses of 10, 25, 50, and 100 μg/rabbit/day (Tables 7 and 8). By the sc route, 6α-methyl-17α-ethynylprogesterone was approximately 20 to 40 times as potent as progesterone (Table 8). When given orally, 6α-methyl-17α-ethynylprogesterone was four times more potent than progesterone administered subcutaneously (Table 7). Further, 6α-methyl-17α-ethynylprogesterone was at least as twice as potent as 6α-methyl-17-acetoxyprogesterone (Provera ®) when both compounds were given orally (Table 7).

6-Methyl-6-dehydro-17α-ethynylprogesterone was evaluated in the Clauberg Assay at oral doses of 5, 10, 25 and 50 μg/rabbit/day (Table 9). By the oral route, this compound was more than eight times as potent as progesterone administered subcutaneously. In addition, 6-methyl-6-dehydro-17α-ethynylprogesterone proved to be equipotent with levonorgestrel when both compounds were given orally (Table 9).

TABLE 5

Oral Progestational Activity of 17α-Ethynylprogesterone, Levonorgestrel, and Medroxyprogesterone Acetate (Provera ®) in the Clauberg Assay*

| Compound | Daily Dose** (μg/rabbit) | Uterine Weight (g) (X ± S.D.) | McPhail Index (0–4) |
|---|---|---|---|
| Control (oral) | 0.5 ml peanut oil | 1.27 ± 0.33 | 0.75 ± 0.54 |
| Progesterone (sc) | 200 | 2.57 ± 0.12 | 4.00 ± 0.00 |
| 17α-Ethynyl-progesterone (oral) | 100 | 1.13 ± 0.24 | 0.25 ± 0.35 |
|  | 200 | 1.67 ± 0.33 | 1.40 ± 1.50 |
|  | 400 | 1.70 ± 0.50 | 1.80 ± 1.70 |
| Levonorgestrel (oral) | 100 | 3.57 ± 1.08 | 3.90 ± 0.12 |
|  | 200 | 2.80 ± 0.14 | 4.00 ± 0.00 |
|  | 400 | 2.67 ± 0.80 | 3.70 ± 0.47 |
| Medroxyprogesterone Acetate (oral) | 100 | 2.65 ± 0.35 | 3.90 ± 0.13 |
|  | 200 | 3.30 ± 0.41 | 4.00 ± 0.00 |
|  | 400 | 3.73 ± 0.61 | 4.00 ± 0.00 |

*This assay employs estrone-primed immature New Zealand White rabbits. For methods refer to Reel et al, Fertility and Sterility 31, 552 (1979).
**This assay utilized three rabbits per dose group. The peanut oil or compound was administered by the route indicated.

TABLE 6

Progestational Activity of 5α-Dihydro-17α-Ethynylprogesterone in the Clauberg Assay*

| Compound | Daily Dose** (μg/rabbit) | Uterine Weight (g) (X ± S.D.) | McPhail Index (0–4) |
|---|---|---|---|
| Control (sc) | 0.5 ml peanut oil | 1.17 ± 0.17 | 0.08 ± 0.12 |
| Progesterone (sc) | 200 | 3.67 ± 0.50 | 4.00 ± 0.00 |
| 5α-Dihydro-17α-ethynyl-progesterone (sc) (lot 2) | 5 | 0.90 ± 0.29 | 0.08 ± 0.12 |
|  | 10 | 1.33 ± 0.09 | 0.29 ± 0.24 |
|  | 20 | 1.03 ± 0.17 | 0.04 ± 0.06 |
| 5α-Dihydro-7α-ethynyl-progesterone (oral) (lot 2) | 100 | 1.00*** | 0*** |
|  | 200 | 1.30 ± 0.22 | 0.04 ± 0.06 |
|  | 400 | 1.10 ± 0.08 | 0.04 ± 0.06 |

*This assay employs estrone-primed immature New Zealand White rabbits. For methods refer to Reel et al, Fertility and Sterility 31, 552 (1979).
**This assay utilized three rabbits per dose group. The peanut oil or compound was administered by the route indicated.
***At sacrifice one rabbit was found to be a male and one rabbit had one uterine horn. Therefore, the data shown are for the remaining rabbit in this group.

TABLE 7

Progestational Activity of 5α-Dihydro-17α-ethynylprogesterone, 17α-Ethynyl-19-norprogesterone, 6α-Methyl-17α-ethynyl-progesterone, and 6α-Methyl-17α-acetoxy-progesterone (Provera ®) in the Clauberg Assay*

| Compound | Daily Dose** (μg/rabbit) | Uterine Weight (g) (X ± S.D.) | McPhail Index (0–4) (X ± S.D.) |
|---|---|---|---|
| Control (sc) | 0.5 ml peanut oil | 1.32 ± 0.12 | 0.33 ± 0.12 |
| Progesterone (sc) | 200.0 | 3.00 ± 0.93*** | 3.94 ± 0.06*** |
| 5α-Dihydro-17α-ethynyl-progesterone (sc) | 100.0 | 1.18 ± 0.25 | 0.13 ± 0.13 |
|  | 200.0 | 1.15 ± 0.07 | 0.58 ± 0.16 |
|  | 400.0 | 1.24 ± 0.09 | 0.33 ± 0.06 |
| 17α-Ethynyl-19-norprogesterone (orally) | 50.0 | 1.41 ± 0.02 | 0.38 ± 0.27 |
|  | 100.0 | 1.72 ± 0.36 | 1.17 ± 1.10 |
|  | 200.0 | 1.70 ± 0.33 | 0.83 ± 0.72 |
|  | 400.0 | 3.40 ± 1.14 | 3.75 ± 0.10 |
| 6α-Methyl-17α-ethynyl-progesterone (orally) | 10.0 | 1.28 ± 0.37 | 0.67 ± 0.42 |
|  | 25.0 | 2.43 ± 0.41 | 2.67 ± 1.00 |
|  | 50.0 | 3.21 ± 0.79 | 3.92 ± 0.12 |
|  | 100.0 | 3.28 ± 0.35 | 4.00 ± 0.00 |
| 6α-Methyl-17α-acetoxy-progesterone (orally) | 5.0 | 1.08 ± 0.01 | 0.29 ± 0.06 |
|  | 10.0 | 1.35 ± 0.34 | 0.71 ± 0.06 |
|  | 25.0 | 1.12 ± 0.19 | 0.25 ± 0.10 |
|  | 50.0 | 2.82 ± 0.92 | 3.00 ± 0.83 |
|  | 100.0 | 2.11 ± 1.28 | 2.66 ± 1.10 |

*This assay employs estrone-primed immature New Zealand White rabbits. For methods refer to Reel et al., Fertility and Sterility 31, 552, 1979.
**This assay utilized three rabbits per dose group. Peanut oil or compound was administered by the route indicated.
***One rabbit in this group died during the dosing period. The data shown are for the remaining two animals in this group.

TABLE 8

Progestational Activity of 17α-Ethynyl-19-norprogesterone and 6α-Methyl-17α-ethynylprogesterone in the Clauberg Assay*

| Compound | Daily Dose** (μg/rabbit) | Uterine Weight (g) (X ± S.D.) | McPhail Index (0–4) (X ± S.D.) |
|---|---|---|---|
| Control (sc) | 0.5 ml peanut oil | 0.67*** | 0*** |
| Progesterone | 200.0 | 1.72 ± 0.14*** | 2.80 ± 0.20**** |
| 17α-Ethynyl 19-norprogesterone (sc) | 2.5 | 2.64 ± 0.22 | 3.25 ± 0.41 |
|  | 5.0 | 3.55 ± 0.54 | 3.97 ± 0.05 |
|  | 10.0 | 4.57 ± 0.67 | 3.92 ± 0.12 |

TABLE 8-continued

Progestational Activity of 17α-Ethynyl-
19-norprogesterone and 6α-Methyl-
17α-ethynylprogesterone in the Clauberg
Assay*

| Compound | Daily Dose** (μg/rabbit) | Uterine Weight (g) (X ± S.D.) | McPhail Index (0-4) (X ± S.D.) |
|---|---|---|---|
|  | 20.0 | 4.94 ± 0.87 | 4.00 ± 0.00 |
| 6α-Methyl- | 2.5 | 1.31 ± 0.20 | 0.21 ± 0.06 |
| 17α-ethynyl- | 5.0 | 1.84 ± 0.48 | 1.29 ± 1.40 |
| progesterone | 10.0 | 3.68 ± 0.31 | 3.92 ± 0.12 |
| (sc) | 20.0 | 3.69 ± 0.62 | 4.00 ± 0.00 |

*This assay employs estrone-primed immature New Zealand White Rabbits. For methods refer to Reel et al., Fertility and Sterility 31, 552, 1979.
**This assay utilized three rabbits per dose group. Peanut oil or compound was administered by the subcutaneous (sc) route.
***One rabbit died during the quarantine period and at necropsy one rabbit had no ovaries and only one atrophic uterine horn. The data shown are for the remaining animal in this group.
****One rabbit in this group died during the quarantine period. The data shown are for the remaining two animals in this group.

TABLE 9

Progestational Activity of 6-Methyl-6-
dehydro-17α-ethynylprogesterone and
Levonorgestrel in the Clauberg Assay*

| Compound | Daily Dose** (μg/rabbit) | Uterine Weight (g) (X ± S.D.) | McPhail Index (0-4) (X ± S.D.) |
|---|---|---|---|
| Control (orally) | 0.5 ml peanut oil | 1.08 ± 0.51 | 0.13 ± 0.18 |
| Progesterone | 200.0 | 1.65 ± 0.30 | 1.79 ± 0.50 |
| 6-Methyl-6- | 5.0 | 0.99 ± 0.34 | 0.00 ± 0.0 |
| dehydro-17α- | 10.0 | 1.11 ± 0.23 | 0.17 ± 0.12 |
| ethynyl- | 25.0 | 2.93 ± 1.33 | 3.33 ± 0.62 |
| progesterone (orally) | 50.0 | 3.59 ± 0.43 | 4.00 ± 0.00 |
| Levonogestrel | 5.0 | 1.30 ± 0.49 | 0.08 ± 0.12 |
| (orally) | 10.0 | 0.86 ± 0.04 | 0.04 ± 0.06 |
|  | 25.0 | 2.59 ± 0.81 | 3.71 ± 0.16 |
|  | 50.0 | 1.95 ± 0.41 | 2.92 ± 0.42 |

*This assay employs estrone-primed immature New Zealand White rabbits. For methods refer to Reel et al., Fertility and Sterility 31, 552, 1979.
**This assay utilized three rabbits per dose group. Peanut oil or compound was administered by the route indicated.

Dosage Levels

The pharmacological activity of several progestogens in women and laboratory animals has recently been elegantly summarized [F. Neumann, Postgrad. Med. J. 54 (Suppl. 2), 11–24, 1978]. The progestational potency for a given compound was shown to be highly comparable in the Kaufman test (endometrial transformation in estrogen-primed ovariectomized or climacteric women) and the Clauberg assay (estrogen-primed immature rabbits). Threshold or effective doses for representative examples from Table 3 of Neumann (1978) are shown below:

| Progestogen | Clauberg Assay (mg/animal) oral | s.c. (i.m.) | Kaufman Assay (mg/cycle) oral |
|---|---|---|---|
| Progesterone | 10.0 | 0.5 | 200 (i.m.) |
| Norethisterone | 0.1–03 | 0.1 | 100–150 |
| (±)Norgestrel | 0.03–0.1 | 0.03 | 12 |
| Levonorgestrel | 0.03 | 0.01–0.03 | 6 |
| Norethynodrel | 0.3 | 0.3 | 150–200 |
| Medroxyprogesterone Acetate | 0.01–0.03 | 0.01–0.03 | 40–70 |
| Megestrol Acetate | 0.03 | 0.01–0.03 | 35–50 |

Combination oral contraceptives contain 0.5 to 2.5 mg of progestogen, whereas progestogen only oral contraceptives have 0.35 mg of active compound (J. E. Huff and L. Hernandez, J. Amer. Pharmaceut. Assoc. NS14, 244–251, 1974). The long-acting injectable contraceptive Noristat ® (Schering A. G., norethindrone enanthate) is given i.m. in 200 mg doses every eight weeks, while Depo-Provera ® (Upjohn, medroxyprogesterone acetate) is injected i.m. at 300 mg every six months or at 150 mg every three months [Beck et al., In: *Research Frontiers in Fertility Regulation*, G. I. Zatuchi (ed.), Vol. 1, No. 1, 1980, pp. 1–16; Nash, H. A., Contraception 12, 377–393, 1975]. Provera ® (Upjohn, medroxyprogesterone acetate) is taken daily as 10 mg tablets in order to treat secondary amenorrhea or abnormal uterine bleeding due to hormonal imbalance (*Physician's Desk Reference*, 1980, p. 1784).

Megace ® (Mead-Johnson, megestrol acetate) is utilized for the palliative treatment of advanced carcinoma of the breast and endometrium. The recommended dosage for breast cancer is 160 mg/day (40 mg tablets, q.i.d.) and that for endometrial carcinoma is 40 to 320 mg/day, given in divided doses (*Physician's Desk Reference*, 1980, p. 1116). Experimentally, 12 endometrial cancer patients were given a single injection of 80 mg of polyestradiol phosphate and subsequently nine received i.m. injections of 1250 mg of 17α-hydroxyprogesterone caproate twice weekly and three received 300 mg of 19-nor-17α-hydroxyprogesterone caproate twice weekly for periods of three to seven weeks. Significant inhibition of nucleic acid synthesis was found in curettage specimens from all 12 patients, thereby demonstrating the effectiveness of this treatment regimen [Norqvist, S., In: *Endometrial Cancer*, Brush, M. G., R. W. Taylor and D. C. Williams (eds.), William Heinemann Medical Books, Ltd., Lond, 1973, p. 33].

Based on this limited number of examples, the range of human progestational dosages is 0.007 mg/kg to 25 mg/kg, and this is the range contemplated for use with the present invention.

Blockade of Ovulation in Rats by Progesterone and 17α-Ethynylprogesterone—The assay procedures of Beattie and Corbin, [Endocrinology 97, 885 (1975)] were employed to evaluate the blockade of ovulation in rats by progesterone and 17α-ethynylprogesterone. Cycling rats were given a single sc injection of 0.2 ml peanut oil (controls), 100, 250, or 500 μg progesterone or 50, 100, 250 or 500 μg 17α-ethynylprogesterone at 1330 hr on diestrus. The treated rats were sacrificed on the morning of expected estrus and eggs, if present, were flushed from the oviducts and counted.

All five rats injected with peanut oil ovulated a normal complement of eggs (Table 10). Similarly, animals treated with 100 or 250 μg progesterone or 50 μg 17α-ethynylprogesterone ovulated in a normal fashion. In contrast, ovulation was blocked in most rats given either 500 μg progesterone or 100, 250 or 500 μg 17α-ethynylprogesterone (Table 10). These data imply that 17α-ethynylprogesterone was about five times as potent as progesterone in blocking ovulation in rats. In the study of Beattie and Corbin [Endocrinology 97, 885 (1975)], (±)-norgestrel also was five times as effective as progesterone in suppressing ovulation. Hence, in this assay 17α-ethynylprogesterone appeared to be equipotent with (±)-norgestrel.

TABLE 10

Blockade of Ovulation in Rats by Progesterone and 17α-Ethynylprogesterone*

| Compound | Dose** (μg/rat) | No. Rat Treated | No. Rats Ovulated | No. of Oviductal Eggs in Rats that Ovulated (X ± S.D.) |
|---|---|---|---|---|
| Control | 0.2 ml peanut oil | 5/5 | | 9.2 ± 3.8 |
| progesterone (sc) | 100.0 | 5/5 | | 7.8 ± 3.8 |
| | 250.0 | 4/5 | | 7.0 ± 3.8 |
| | 500.0 | 1/4 | | 9.0 |
| 17α-Ethynyl-progesterone (sc) | 50.0 | 4/5 | | 10.5 ± 2.1 |
| | 100.0 | 1/5 | | 3.0 |
| | 250.0 | 1/5 | | 6.0 |
| | 500.0 | 0/5 | | 0.0 |

*This assay employs cycling Charles River CD rats. For methods refer to Beattie, C. W. and A. Corbin, Endocrinology 97, 885, 1975.
**Groups of rats (5/group) were given a single sc injection of 0.2 ml peanut oil (control) or compound (in 0.2 ml peanut oil) at 1330 hr on diestrus. Rats were sacrificed 43 to 44 hr later on the morning of expected estrus. Eggs, if present, were flushed from oviducts and counted under a stereomicroscope.

Suppression of Estrous Cycles in Rats by 17α-Ethynylprogesterone—Groups of five rats each showing two consecutive four-day estrous cycles as determined by vaginal smears were injected sc daily for 10 days with 50, 100, 250 or 500 μg of 17α-ethynylprogesterone. A control group was treated in parallel with 0.2 ml peanut oil per day. Treatment commenced at metestrus and vaginal smears were taken each morning during the 10-day treatment period and for 16 to 18 days thereafter.

All rats in the control and 50 μg 17α-ethynylprogesterone/day groups continued regular four-day cycles during treatment, whereas estrous cycles were disrupted in rats treated with 100, 250 or 500 μg 17α-ethynylprogesterone/day. The animals given 100 μg 17α-ethynylprogesterone/day progressed to proestrus by the third or fourth day of treatment, but estrus did not follow proestrus as in the normal cycle. Rather, the vaginal smear pattern observed for the next two or three days was consistent with a metestrous-diestrous state. This is turn was followed again by a proestrous and then a metestrous-diestrous state for the remaining two or three days of treatment. These results indicated that some degree of follicular development occurred, but that ovulation was inhibited during treatment. That the effects of 17α-ethynylprogesterone were reversible was indicated by the fact that the animals resumed regular estrous cycles within 2 to 10 days (appearance of estrus) after treatment. A similar estrous cycle pattern was observed during treatment with 250 μg 17α-ethynylprogesterone/day, however, regular estrous cycles resumed more slowly (7 to 12 days) following treatment than in the case of 100 μg 17α-ethynylprogesterone/day.

The effects of 500 μg 17α-ethynylprogesterone/day on the estrous cycle were more dramatic than at the lower doses of the compound. Throughout the 10-day treatment period the animals remained predominantly in a diesterous state suggesting that follicular development and ovulation were effectively suppressed. Normal four-day estrous cycles resumed in all animals 7 to 12 days after discontinuing treatment.

Anti-androgenic Activity

The oral anti-androgenic activity of 6-methyl-6-dehydro-17α-ethynylprogesterone was evaluated in the castrate immature male rat assay [Lerner et al., Proc. Soc. Exp. Biol. Med. 103, 172 (1960)]. The assay is briefly described in the footnotes to Table 11. When given orally (400 μg/rat/day) for seven days concurrently with subcutaneously administered testosterone (400 μg/rat/day), 6-methyl-6-dehydro-17α-ethynylprogesterone exhibited anti-androgenic activity as indicated by a significant depression of ventral prostate weight (Table 11). Seminal vesicle weight also was depressed at the same dose level, but the decrease was not statistically significant. At similar oral doses, megestrol acetate also exhibited significant anti-androgenic activity. In contrast, subcutaneously administered progesterone was inactive at daily doses as high as 400 μg/rat/day (Table 11).

TABLE 11

Anti-androgenic Activity of 6-Methyl-6-dehydro-17α-ethylprogesterone and 6-Methyl-6-dehydro-17α-acetoxyprogesterone (Megestrol Acetate) in the Castrate Immature Rat Assay*

| Compound | Daily Dose** (μg/rat) | Ventral Prostate (mg) (X ± S.D.) | Seminal Vesicles (mg) (X ± S.D.) | Levator Ani (mg) (X ± S.D.) |
|---|---|---|---|---|
| Control (sc) | 0.3 ml sesame oil | 9 ± 3 | 12 ± 3 | 32 ± 8 |
| Testosterone (sc) | 25.0 | 18 + 5 | 23 ± 12 | 36 ± 4 |
| Testosterone (sc) | 100.0 | 35 ± 5 | 66 ± 6 | 53 ± 6 |
| Testosterone (sc) | 400.0 | 70 ± 22 | 163 ± 43 | 63 ± 14 |
| Testosterone (sc) + Progesterone (sc) | 400.0 25.0 | 71 ± 28 | 157 ± 19 | 54 ± 15 |
| Testosterone (sc) + Progesterone (sc) | 400.0 100.0 | 80 ± 27 | 145 ± 17 | 58 ± 15 |
| Testosterone (sc) + Progesterone (sc) | 400.0 400.0 | 60 ± 26 | 162 ± 26 | 59 ± 14 |
| Testosterone (sc) + 6-Methyl-6-dehydro-17α-ethynyl-progesterone (orally) | 400.0 25.0 | 61 ± 13 | 141 ± 43 | 63 ± 13 |
| Testosterone (sc) + 6-Methyl-6-dehydro-17α-ethynyl-progesterone (orally) | 400.0 100.0 | 63 ± 25 | 141 ± 9 | 68 ± 13 |
| Testosterone (sc) + 6-Methyl-6-dehydro-17α-ethynyl-progesterone (orally) | 400.0 400.0 | 43 ± 12*** | 129 ± 37 | 66 ± 9 |
| Testosterone (sc) + Megestrol Acetate (orally) | 400.0 25.0 | 42 ± 20*** | 125 ± 23*** | 50 ± 8 |
| Testosterone (sc) + Megestrol Acetate (orally) | 400.0 100.0 | 54 ± 13 | 128 ± 36 | 55 ± 12 |
| Testosterone (sc) + | 400.0 | 48 ± 15*** | 120 ± 21*** | 65 ± 12 |

TABLE 11-continued

Anti-androgenic Activity of 6-Methyl-6-dehydro-17α-ethylprogesterone and 6-Methyl-6-dehydro-17α-acetoxyprogesterone (Megestrol Acetate) in the Castrate Immature Rat Assay*

| Compound | Daily Dose** (μg/rat) | Ventral Prostate (mg) ($\bar{X} \pm$ S.D.) | Seminal Vesicles (mg) ($\bar{X} \pm$ S.D.) | Levator Ani (mg) ($\bar{X} \pm$ S.D.) |
|---|---|---|---|---|
| Megestrol Acetate (orally) | 400.0 | | | |

*This assay employs castrate immature rats. For methods refer to Lerner, L. J., A. Bianchi and A. Borman, Proc. Soc. Exp. Biol. Med. 103, 172, 1960.

**Groups of rats (7/group) were given daily injections of 0.3 ml sesame oil (control) or compound (in 0.3 ml sesame oil) for 7 days. Some groups also concurrently received progestational compounds by the sc or oral route of administration in order to evaluate anti-androgenic activity. One day after the final doses, the animals were sacrificed and the androgen target organs indicated were weighed.

***Statistically significant (p < 0.05) lower organ weights versus the testosterone, sc, (400 μg/rat/day) group as determined by Analysis of Variance coupled with Duncan's Multiple Range Test. These significantly lower organ weights indicate clear-cut anti-androgenic activity.

What is claimed is:
1. Derivatives of 17α-ethynylpregnane-20-one.
2. A steroid selected from the group consisting of
(a) a steroid having the formula

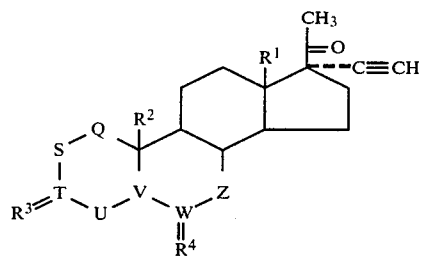

and
(b) a steroid having the formula

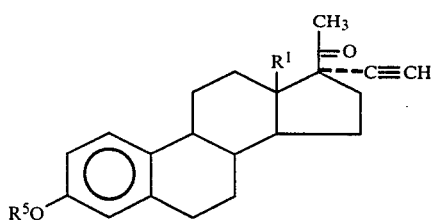

wherein
$R^1$ is selected from the group consisting of methyl, ethyl, and propyl;
$R^2$ is selected from the group consisting of H and methyl;
$R^3$ is selected from the group consisting of OXO and H(OR$^5$);

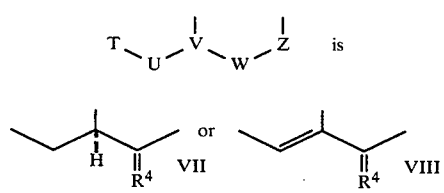 is

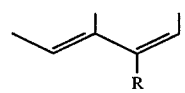

wherein;
R is selected from the group consisting of H, methyl, Cl, and F;
$R^5$ is H or a pharmaceutically acceptable substituent selected from the group consisting of:
acyl having from 1 to 12 carbon atoms,
2-tetrahydropyranyl, 4-tetrahydropyranyl,
1-cycloalkyl having from 5 to 7 carbon atoms,
1-methoxycycloalkyl and 1-ethoxycycloalkyl in which the cycloalkyl group has from 5 to 7 carbon atoms,
cycloalkylcarbonyl wherein the cycloalkyl group has from 5 to 10 carbon atoms,
benzoyl, phenacetyl, 1-adamantylcarbonyl, and 1-cyclopentylcarbonyl; and
Q-S is CH=CH— or —CH$_2$—CH$_2$—.

3. A steroid as claimed in claim 2, having the formula:

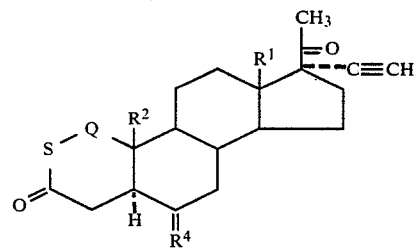

wherein
$R^1$ is methyl, ethyl or propyl,
$R^2$ is H or methyl,
$R^4$ is H$_2$, H(methyl), H(Cl), or H(F), and
S-Q is —CH=CH— or —CH$_2$—CH$_2$—.

4. A steroid as claimed in claim 3, wherein said steroid is 17α-ethynyl-5α-pregnane-3,20-dione.

5. A steroid as claimed in claim 3, wherein said steroid is 17α-ethynyl-19-nor-5α-pregnane-3,20-dione.

6. A steroid as claimed in claim 2, having the formula

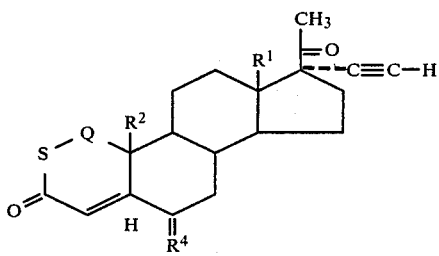

wherein $R^1$ is methyl, ethyl, or propyl,
$R^2$ is H or methyl,
$R^4$ is $H_2$, H(methyl), H(Cl), H(F), or $=CH_2$, and
S-Q is $-CH=CH-$ or $-CH_2-CH_2-$.

7. A steroid as claimed in claim 6, wherein said steroid is 17α-ethynyl-4-pregnene-3,20-dione.

8. A steroid as claimed in claim 6, wherein said steroid is 17α-ethynyl-19-nor-4-pregnene-3,20-dione.

9. A steroid as claimed in claim 6, wherein said steroid is 17α-ethynyl-6α-methyl-4-pregnene-3,20-dione.

10. A steroid as claimed in claim 6, wherein said steroid is 17α-ethynyl-6-methyleneprogesterone.

11. A steroid as claimed in claim 6, wherein said steroid is 17α-ethynyl-6-methylene-19-norprogesterone.

12. A steroid as claimed in claim 2, having the formula

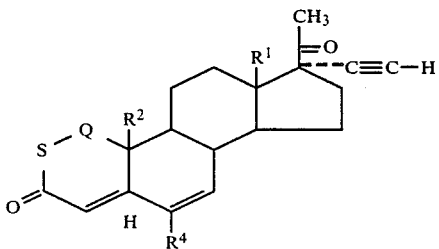

wherein $R^1$ is methyl, ethyl, or propyl,
$R^2$ is H or methyl,
$R^4$ is H, methyl, Cl, or F, and
S-Q is $-CH=CH-$ or $-CH_2-CH_2-$.

13. A steroid as claimed in claim 12, wherein said steroid is 17α-ethynyl-6-methyl-4,6-pregnadiene-3,20-dione.

14. A method of inducing a progestational response in a mammal, comprising administering to said mammal an effective amount of a compound exhibiting progestational activity, said compound having the formula

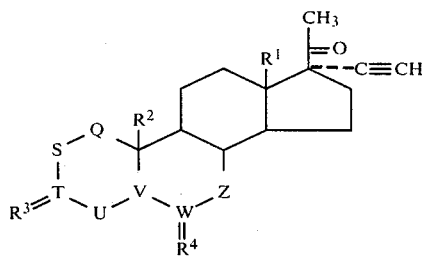

wherein $R^1$ is selected from the group consisting of methyl, ethyl, and propyl;
$R^2$ is selected from the group consisting of H and methyl;
$R^3$ is selected from the group consisting of OXO and $H(OR^5)$;

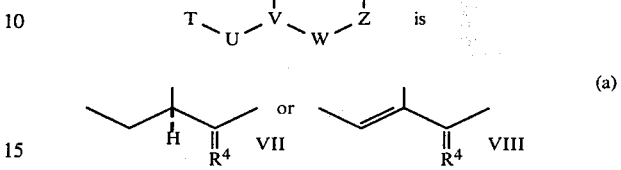

wherein $R^4$ is selected from the group consisting of $H_2$, H(methyl), H(Cl), H(F), and $=CH_2$; or

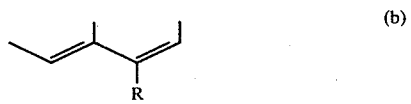

wherein

R is selected from the group consisting of H, methyl, Cl, and F; and
Q-S is selected from the group consisting of $-CH=CH-$ and $-CH_2-CH_2-$.

15. The method of claim 14 wherein said steroid is selected from the group consisting of

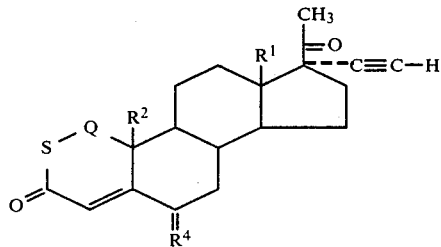

and

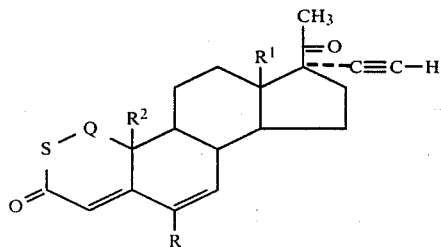

wherein $R^1$ is methyl, ethyl, or propyl,
$R^2$ is H or methyl,
$R^4$ is $H_2$, H(methyl), H(Cl), or H(F),
R is H, methyl, Cl, or F, and
S-Q is $-CH=CH-$ or $-CH_2-CH_2-$.

16. The method of claim 14 wherein said induced progestational response is to control fertility, control estrus, effect hormone replacement, correct hormonal imbalance, or treat steroid-responsive hyperplasias and tumors.

17. The method of claim 15, wherein said steroid is 17α-ethynyl-4-pregnene-3,20-dione.

18. The method of claim 15, wherein said steroid is 17α-ethynyl-19-nor-4-pregnene-3,20-dione.

19. The method of claim 15, wherein said steroid is 17α-ethynyl-6α-methyl-4-pregnene-3,20-dione.

20. The method of claim 15, wherein said steroid is 17α-ethynyl-6-methylene-progesterone.

21. The method of claim 15, wherein said steroid is 17α-ethynyl-6-methylene-19-norprogesterone.

22. The method of claim 15, wherein said steroid is 17α-ethynyl-6-methyl-4,6-pregnadiene-3,20-dione.

23. The method of claim 15, wherein said mammal is a farm animal.

24. The method of claim 15, wherein said mammal is a domestic pet.

25. The method of claim 15, wherein said hormonal imbalance is clinically manifested as secondary amenorrhea.

26. The method of claim 15, wherein said steroid is administered parenterally in an amount between about 0.007 and 25 mg per kilogram of body weight.

27. The method of claim 15 wherein said steroid is administered orally in an amount between about 0.007 and 25 mg per kilogram of body weight.

28. The method of claim 15, wherein said steroid is administered orally in conjunction with an estrogen.

29. The method of claim 28, wherein said estrogen is ethinyl estradiol.

30. A steroid selected from the group consisting of
(a) a steroid having the formula

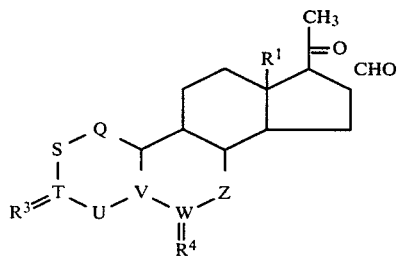

and
(b) a steroid having the formula

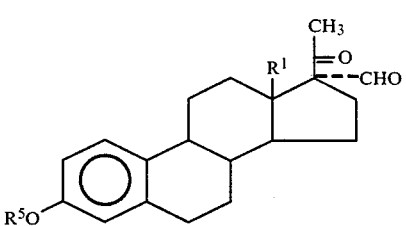

wherein
R¹ is selected from the group consisting of methyl, ethyl, and propyl;
R² is selected from the group consisting of H and methyl;
R³ is selected from the group consisting of OXO and H(OR⁵);

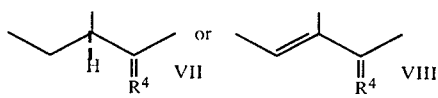

wherein
R⁴ is selected from the group consisting of H₂, H(methyl), H(Cl), H(F), and CH₂; or

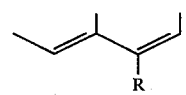

wherein
R is selected from the group consisting of H, methyl, Cl, and F;
R⁵ is H or a pharmaceutically acceptable substituent selected from the group consisting of:
acyl having from 1 to 12 carbon atoms,
2-tetrahydropyranyl, 4-tetrahydropyranyl,
1-cycloalkyl having from 5 to 7 carbon atoms,
1-methoxycycloalkyl and 1-ethoxycycloalkyl in which the cycloalkyl group has from 5 to 7 carbon atoms,
cycloalkylcarbonyl wherein the cycloalkyl group has from 5 to 10 carbon atoms,
benzoyl, phenacetyl, 1-adamantylcarbonyl, and 1-cyclopentylcarbonyl; and
Q-S is CH=CH— or —CH₂—CH₂—.

31. A steroid as claimed in claim 30, wherein said steroid is 17α-formylprogesterone.

32. A steroid as claimed in claim 30, wherein said steroid is 17α-formyl-19-norprogesterone.

33. A steroid as claimed in claim 30, wherein said steroid is 17α-formyl-6α-methylprogesterone.

34. A steroid as claimed in claim 30, wherein said steroid is 17α-formyl-6-methylpregna-4,6-dien-3-one.

35. A steroid as claimed in claim 30, wherein said steroid is 17α-formyl-3-methoxy-19norpregna-1,3,5(10)-trien-20-one.

36. A steroid as claimed in claim 30, wherein said steroid is 17α-formyl-5α-pregnane-3,20-dione.

37. A steroid as claimed in claim 30, wherein said steroid is 17α-formyl-19-nor-5α-pregnane-3,20-dione.

38. A steroid as claimed in claim 30, wherein said steroid is 17α-ethynyl-3-methoxy-19-norpregna-1,3,5(10)-trien-20-one.

39. A composition comprising a progestationally active steroid as defined in claim 2 and a pharmaceutically acceptable carrier.

40. A method of preparing derivatives of 17α-ethynylpregnane-20-one, comprising:
oxidizing a 17α-hydroxymethylpregnane-20-one derivative to the corresponding 17α-formylpregnane-20-one derivative; and
transforming said 17α-formylpregnane-20-one derivative to said 17α-ethynylpregnane-20-one derivative.

41. The method of claim 40, wherein said 17α-formyl-pregnane-20-one derivative is reacted with O,O dimethyl diazomethylphosphonate in the presence of potassium tert-butoxide and in an anhydrous solvent.

* * * * *

UNITED STATES PATENT AND TRADEMARK OFFICE
CERTIFICATE OF CORRECTION

PATENT NO. : 4,512,986
DATED : April 23, 1985
INVENTOR(S) : REEL

It is certified that error appears in the above-identified patent and that said Letters Patent is hereby corrected as shown below:

The title should read "PROGESTATIONALLY ACTIVE STEROIDS", rather than "PROGRESTATIONALLY ACTIVE STEROIDS". This error appears on the title page and again at column 1, line 1.

Column 4, line 58 should read "to denote two hydrogen...," rather than "to denote to hydrogen..."

Steroid structure (4) in column 8, lines 43-44, should have two dots connecting the lower capital H with the steroid nucleus.

Column 9, line 32 should be "hydrochloric", rather than "hydrochloride".

Column 9, lines 50 and 51 should read "...dilution with distilled $H_2O$..." rather than "...dilution was distilled $H_2O$..."

UNITED STATES PATENT AND TRADEMARK OFFICE
CERTIFICATE OF CORRECTION

PATENT NO. : 4,512,986
DATED : April 23, 1985
INVENTOR(S) : REEL

It is certified that error appears in the above—identified patent and that said Letters Patent is hereby corrected as shown below:

Column 14, line 55 should read "...derivatives...", rather than "derivaties".

Column 25, line 21 should read "17α-ethynylpregnan-20-one", rather than "17α-ethynylpregnane-20-one." (There should not be an "e" at the end of pregnan.)

Column 27, line 10, there is an extraneous capital H at the bottom of the structure.

Signed and Sealed this

First Day of October 1985

[SEAL]

Attest:

DONALD J. QUIGG

Attesting Officer

Commissioner of Patents and Trademarks—Designate